Figure 1:
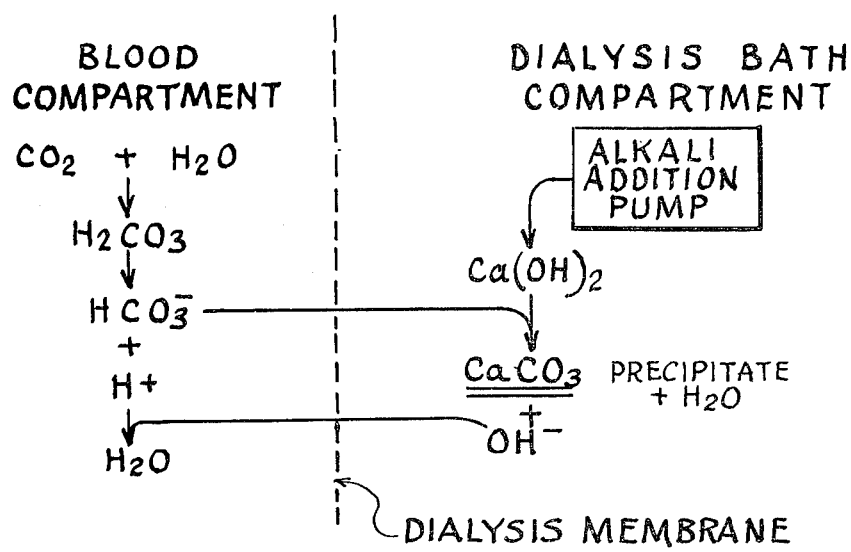

United States Patent [19]
Updike

[11] 3,953,329
[45] Apr. 27, 1976

[54] METHOD FOR DIALYZING CARBON DIOXIDE FROM BLOOD PLASMA

[75] Inventor: Stuart J. Updike, Madison, Wis.

[73] Assignee: Wisconsin Alumni Research Foundation, Madison, Wis.

[22] Filed: Oct. 5, 1972

[21] Appl. No.: 295,264

Related U.S. Application Data

[63] Continuation-in-part of Ser. No. 191,720, Oct. 22, 1972, Pat. No. 3,846,236.

[52] U.S. Cl. .................. 210/22 R; 128/214 R; 128/DIG. 3; 195/1.7; 195/1.8
[51] Int. Cl.² ................. B01D 13/00; C12B 1/00
[58] Field of Search ............. 195/1.8; 23/258.5; 128/214 R; 210/22, 321

[56] References Cited
UNITED STATES PATENTS

| 3,482,575 | 12/1969 | Claff et al. | 23/258.5 |
| 3,743,480 | 7/1973 | Falk | 195/1.8 |

OTHER PUBLICATIONS

Smith, Biochemical Journal, Vol. 28, pp. 1015–1023, 1934.

*Primary Examiner*—Sam Rosen
*Attorney, Agent, or Firm*—McDougall, Hersh & Scott

[57] ABSTRACT

The removal of carbon dioxide from blood plasma by transport through a dialysis membrane in the form of bicarbonate ion, in which the electrolyte supplies hydroxyl ion for transport back through the membrane for maintaining normal blood pH.

10 Claims, 3 Drawing Figures

HEMODIALYSIS OF CARBON DIOXIDE

CARBON DIOXIDE EXCRETION SYSTEM

EXCRETION BY HEMODIALYSIS

METHOD FOR DIALYZING CARBON DIOXIDE FROM BLOOD PLASMA

The invention described herein was made in the course of work under a grant or award from the Department of Health, Education, and Welfare.

This application is a continuation-in-part of my copending application Ser. No. 191,720, filed Oct. 22, 1971, and entitled "Method and Apparatus for Dialysis", now U.S. Pat. No. 3,846,236.

In my copending application, description is made of a method, means and apparatus which makes use of a hemodialysis membrane having entrapped therein a catalyst for conversion of hydrogen peroxide ($H_2O_2$) into water ($H_2O$) and oxygen ($O_2$) during transport of hydrogen peroxide therethrough from dilute solution on one side of the membrane to make nascent oxygen available to the blood plasma or other chemical solution wetting the opposite side of the membrane. For this purpose, the dialyzing oxygenator makes use of a semi-permeable membrane formulated of such materials as cellophane, cellulose acetate, cellulose propionate, insolubilized gelatin, partially hydrolyzed polyvinyl acetate, polyionic films such as formed of polysulfonated anionic polymers, multi-hollow fibers, such as of the type produced by Dow Chemical Company, and silicone rubber or other semi-permeable membranes which are at least partially wettable by the hydrogen peroxide solution and/or the blood plasma or other fluid on the opposite side of the membrane.

As the catalyst, use is preferably made of manganese dioxide formed in situ in the membrane by reaction of a soluble permanganate, such as potassium permanganate, and a reducing agent, such as sodium or other alkali metal iodide, introduced from opposite sides of the membrane. Instead of manganese dioxide, use can be made of other catalyst entrapped within the membrane, such as other metal oxides and hydroxides, such as those of cobalt, nickel, lead, iron and osmium, colloidal silver, colloidal or chelated iron, catalase enzyme or noble metals such as platinum, silver, gold and the like.

Description is also made of the use of the same membrane, or other semi-permeable membrane, with or without the catalyzing agent, for dialyzing carbon dioxide from the blood stream, in the form of bicarbonate ion, and the removal of the bicarbonate from the dialyzing solution by bubbling air therethrough to carry off carbon dioxide whereby the concentration of carbon dioxide in the bath can be maintained at a level for continuous and uniform transport of additional bicarbonate from the blood plasma, and whereby the removal of bicarbonate ion in this fashion generates hydroxylion in the dialysis bath which then diffuses into the blood and neutralizes the associated hydrogen ion.

Thus, the invention described and claimed in the aforementioned copending application relates to the treatment of blood plasma or other solution to introduce oxygen, as an oxygenator, and/or to remove carbon dioxide, as bicarbonate, in the same or in separate systems and to the means and apparatus for accomplishing the same.

This invention is addressed to the concept relating to the use of a semi-permeable membrane as a hemodialysis membrane for the removal of carbon dioxide from blood plasma by dialyzing with carbon dioxide in the form of bicarbonate ion to produce a more efficient and effective artificial lung.

Development of an artificial lung which will safely provide total respiratory support for an extended period of time presents a number of problems. Excessive hemolysis, denaturation of plasma protein, microembolism, and disseminated intravascular coagulation have been associated with the use of the artificial lung, but not with the artificial kidney. Presumably this is because the artificial lung requires higher flow rates of blood and more membrane surface area than an artificial kidney.

The partial pressure available to drive oxygen and carbon dioxide across an artificial lung membrane is about 660 and 47 mm. of mercury respectively. The relatively low partial pressure gradient available to drive carbon dioxide excretion requires that the artificial lung be designed with an amount of membrane surface area several times that required for oxygenation (E. C. Pierce and G. P. Pierce, The Influence of Membrane Characteristics and Lung Design on Gas Exchange. J. Surgical Research 3, 67–76, 1963). Therefore, strategy for developing a better artificial lung includes devising a more efficient method of carbon dioxide excretion.

Thus it is an object of this invention to provide a method and means for more rapid excretion of carbon dioxide from blood, whereby use can be made of dialysis membrane of less membrane surface area and it is a related object to produce a method and means for the removal of carbon dioxide in combination with an oxygenator for the introduction of oxygen into the blood plasma, as described in the aforementioned copending application.

Figure 2:
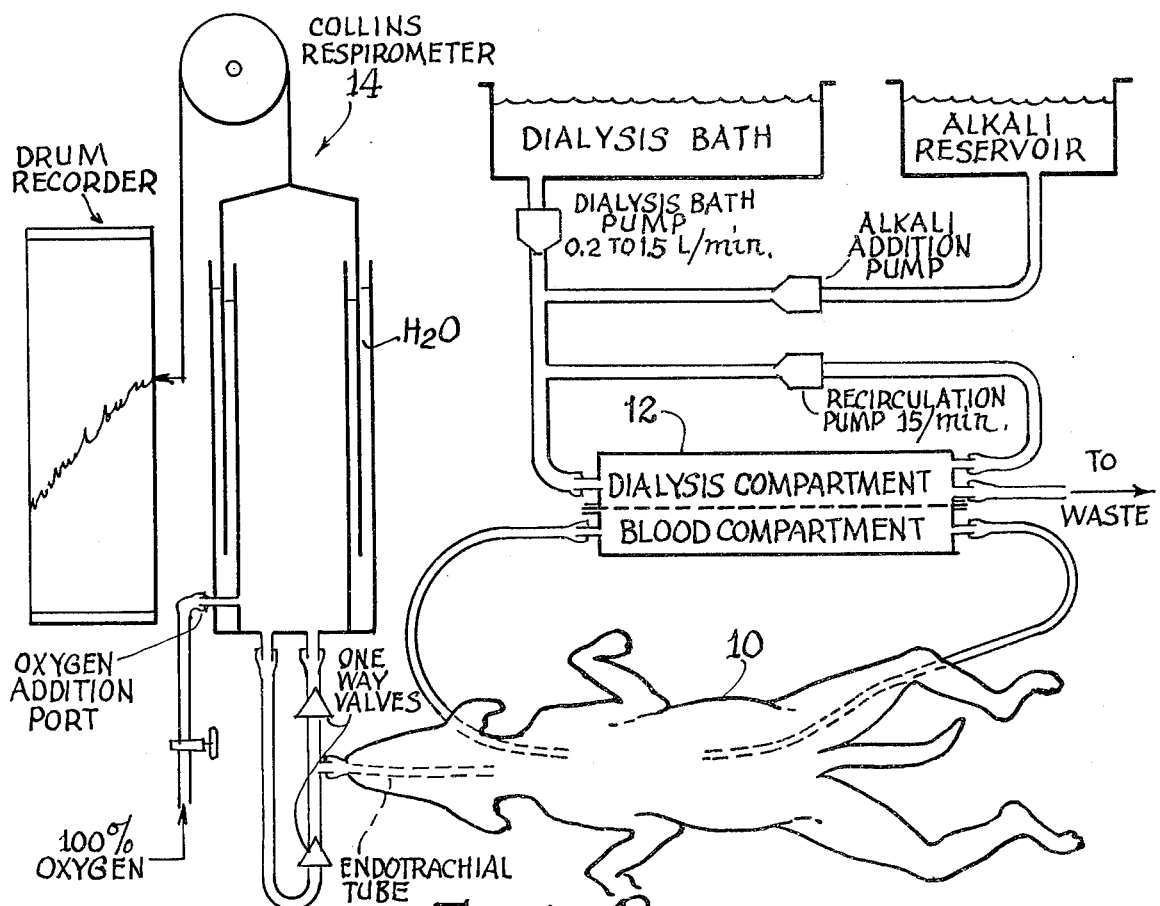
Figure 3:
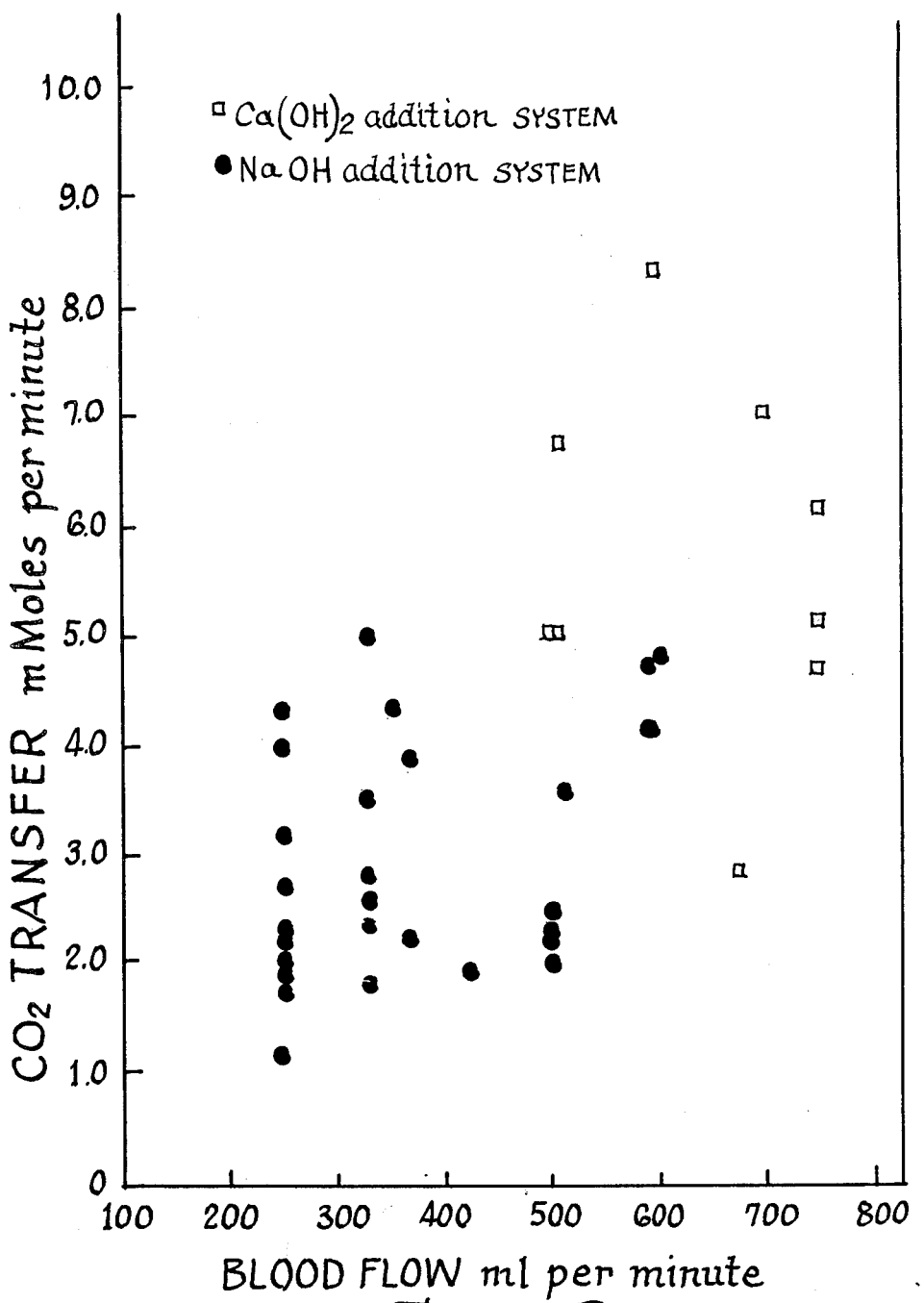

These and other objects and advantages of this invention will hereinafter appear and for purposes of illustration, but not of limitation, an embodiment of the invention is shown in the accompanying drawings in which FIG. 1 is a schematic flow diagram illustrating the practice of this invention;

FIG. 2 is a schematic drawing of a hemodialysis apparatus employed in the experiments for carbon dioxide removal from dogs; and FIG. 3 is a graph showing the carbon dioxide excretion by hemodialysis, secured by the examples described herein.

The method herein is based on excretion of carbon dioxide across a hemodialysis membrane as bicarbonate ion. This system of $CO_2$ excretion is more efficient per unit of membrane surface area because the concentration of bicarbonate ion is normally twenty times greater than the concentration of dissolved $CO_2$. As a result, a more efficient concentration of gradient is available to drive transmembrane excretion of $CO_2$.

Associated with the excretion of bicarbonate ion by hemodialysis is the accumulation of an equivalent amount of buffered hydrogen ion in the blood plasma. In order to maintain a normal blood pH, this amount of hydrogen ion is neutralized by absorption of hydroxyl ion from the dialysis bath. As a result, $CO_2$ excretion by hemodialysis is carried out in accordance with the practice of this invention with the formulation of the dialysis bath to maintain sufficient alkali for hydroxyl ion absorption to neutralize hydrogen ion and to maintain normal blood ph. Thus, as illustrated in the diagram of FIG. 1, sodium hydroxide or calcium hydroxide, or preferably a mixture of both is added to the dialysis bath, preferably continuously or at frequent intervals, in an amount sufficient to maintain acid - base balance.

In general, alkali is added to the bath in an amount to maintain the bath at a pH within the range of 10–13 and preferably within the range of 11–12, corresponding somewhat to 1–10 milli-equivalents of hydroxyl ion per liter. Exact specification of pH of the bath for the rate of alkali addition is somewhat complicated by the fact that glucose and hydrogen peroxide, which are also normally added as a part of the bath, act as hydrogen ion donors at the alkaline pH.

It is more accurate to specify and regulate the additions of alkali by reference to the conditions currently existing with respect to the blood plasma subject to treatment. The desired results can be achieved by monitoring the blood for measurement of blood pH and blood $pCO_2$, both of which are readily measurable by conventional means. These measurements can be made continuously but are preferably made at frequent intervals, such as every five minutes. From these two parameters, the $CO_2$ content of the blood can be determined mathematically by the Henderson-Hasselbalch equation:

$$pH = 6.1 + \log \frac{HCO_3^-}{0.03 \times pCO_2}$$

Both the continuous or intermittent addition of fresh dialysis solution and alkali, preferably in the form of a solution, can be thus regulated to keep the $CO_2$ content of the blood within the broad range of 23–30 millimoles per liter for normal venous blood.

If blood $CO_2$ content increases, then both the addition rate of fresh dialysis bath and the rate of addition of alkali should be increased to return blood $CO_2$ content to normal. Conversely, if blood $CO_2$ decreases, then the addition rate of fresh dialysis bath and alkali should be decreased until $CO_2$ content of the blood is returned to normal.

It is possible for blood $CO_2$ to remain constant while blood pH increases and blood $pCO_2$ decreases, or blood pH decreases while blood $CO_2$ increases. This occurs normally when the patient experiences a "metabolic" rather than "respiratory" acid - base disturbance. Correction for this type of disturbance can be achieved using the following rules:

If blood $pCO_2$ increases, then the addition rate of fresh dialysis solution should be increased until the $pCO_2$ returns to the normal range of 45–58 mm mercury for venous blood. Conversely, if blood $pCO_2$ decreases, then the addition rate of fresh dialysis solution should be decreased until the $pCO_2$ increases into the normal range.

On the other hand, if blood pH falls, then the alkali addition rate should be increased to return blood pH to normal (pH 7.20 – pH 7.35 for venous blood). Conversely, if blood pH increases, then the alkali addition rate should be decreased to return blood pH to within the normal range.

Thus, by appropriately controlling the addition rates of fresh dialysis solution and alkali solution, correction of both metabolic and respiratory disturbances of acid-base balance can be obtained.

Alkali additions can be made by way of solution of a suitable alkali such as an alkali metal hydroxide, preferably sodium hydroxide, or an alkaline earth metal hydroxide, preferably calcium hydroxide or magnesium hydroxide. The addition of sodium hydroxide has the advantage that no precipitate is formed thereby in the dialysis bath. Calcium hydroxide has the advantage that less fresh dialysis solution needs to be added because bicarbonate ion is precipitated in accordance with the following equation:

$$HCO_3^- + Ca(OH)_2 \rightarrow CaCO_3 + H_2O + OH^-$$

A one to one stoichiometric relationship is observed between bicarbonate ion which is dialyzed from the blood and precipitated as calcium carbonate in the bath solution, and hydroxyl ion which is generated in the dialysis bath to be dialyzed into the blood to neutralize the associated buffered hydrogen ion retained in the blood. This stoichiometric relationship is significant because the ratio of bicarbonate ion to hydrogen ion, generated during metabolism, is also one to one, as seen from the following equation:

$$CO_2 + H_2O \rightarrow H_2CO_3 \rightarrow H^+ + HCO_3^-$$

As a result, because of these theoretical stoichiometric relationships, the dialysis bath can be embodied in a closed compartment, except for the addition of calcium hydroxide and the removal of calcium carbonate. The concept of the "closed" dialysis system, whether achieved by addition of calcium hydroxide or by the removal of carbon dioxide by aeration (bubbling air through the bath) is relevant for long term artificial lung treatment where a small closed dialysis compartment would have the advantage of portability, as by eliminating the need for a large reservoir of fresh dialysis solution.

In practice, the over-addition of calcium hydroxide results in calcium carbonate precipitate in the membrane. This can be prevented by formulation to introduce calcium hydroxide in an amount less than the stoichiometric amount needed to precipitate all of the bicarbonate ion as calcium carbonate. Under these circumstances, bicarbonate ion will be present in the bath in excess so that calcium ion is always essentially completely precipitated from the dialysis bath as calcium carbonate and not made available at the membrane for precipitation. This is accomplished by adding an alkali solution formulated essentially of calcium hydroxide, but with sufficient sodium hydroxide so that the calcium ion is substantially completely precipitated from the recirculated dialysis bath. For this purpose, use can be made of an alkali solution as a slurry formulated with the ratio of 2 moles of calcium hydroxide per mole of sodium hydroxide as represented by the addition of one liter of 1.0 M sodium hydroxide to 148 grans of calcium hydroxide. The precipitated calcium carbonate can be removed from the dialysis bath by filtration or sedimentation.

Addition of alkali for pH control can be employed in combination with the removal of carbon dioxide by aeration, as by bubbling air through the bath, as described in the aforementioned copending application, whereby the conversion of the dialyzed bicarbonate ion to water and $CO_2$ produces hydroxyl ions which operate to reduce the amount of alkali required to be added for maintaining the desired pH level and correspondingly reduce the amount of precipitate that is formed. The latter operates to increase the life of the dialysis bath as well as that of the dialysis membrane which may become clogged by entrapment of precipitate. The aeration $CO_2$ removal system corrects only for a respiratory disturbance when used alone. One of the advantages of the alkali addition technique over the aeration $CO_2$ system is that both respiratory and metabolic acid-base disturbances can be corrected in accordance with the practice of this invention. A second advantage is the increased effectiveness of the alkali addition over the $CO_2$ aeration system when the dialysis bath pH is high. Nevertheless, a distinct advantage is derived by the combination of both the alkali addition and aeration, as previously pointed out.

As the dialysis membrane, use can be made of a water wettable membrane of the type previously described, with the entrapped hydrogen peroxide conversion catalyst in the event that simultaneous use is made thereof as an oxygenator with dilute solution of $H_2O_2$, or without entrapped catalyst in the event that the dialysis membrane is used solely to extract carbon dioxide by transport of bicarbonate ion, in accordance with the practice of this invention.

In the modification illustrated by the flow diagram of FIG. 1 for dialysis of human blood plasma, the dialysis bath recipe before addition of alkali was $Na^+$ 135, $Cl^-$ 105, $K^+$ 5, acetate 25 milliequivalents per liter, glucose 250 mg per 100 ml and urea 40 mg per 100 ml of dialysis bath. Either single pass or recirculating single pass configuration of dialysis was used. Both configurations of hemodialysis are well known to those skilled in providing artificial kidney treatment. Addition of alkali was accomplished by saturating the dialysis bath with respect to calcium hydroxide or by interfusion into the dialysis bath of 1.0 N sodium hydroxide to maintain the bath at a pH within the range of 11–12, either of which was effective to maintain normal venous blood pH.

The following examples, which are given by way of illustration and not by way of limitation, represent a number of experiments conducted in the manner shown in FIG. 2 for illustrating the practice of the invention.

For this purpose, a series of 18 mongrel dogs, weighing 10.4 to 21.0 Kg, were anesthetized with 30 mg/Kg of pentobarbital. An endotracheal tube was passed. Each dog was connected to a semi-closed respiratory system and allowed to breathe spontaneously. This ventilatory system was designed so that no carbon dioxide could escape. Thus all exhaled $CO_2$ was rebreathed for the two to four hours duration of the experiment. 100% oxygen was periodically introduced in volumetrically determined amounts. Thus oxygen consumption for the entire experiment could be estimated.

Each dog 10 was placed on vein to vein extracorporeal dialysis using commercially available hemodialysis coils or hollow fiber kidney. Blood was pumped from the inferior vena cava via the femoral vein through the artificial kidney 12 to the superior vena cava via the external jugular vein at flow rates varying from 100 to 750 ml/min. The dog was weighed continuously during the experiment and central venous pressure was continuously monitored. Sufficient lactated Ringer's solution was infused to keep the dog normovolemic. Each dog was heparinized (500 units/Kg initial dose) and donor dog blood was used to prime the artificial kidney.

Oxygen tension, carbon dioxide tension (electrode method), and pH were obtained on venous blood going to and from the artificial kidney every 5 to 10 minutes. The Henderson-Hasselbalch equation was used to calculate total plasma $CO_2$. Total plasma $CO_2$ content was converted to total whole blood $CO_2$ content using the Van Slyke and Sendroy nomogram (D. D. Van Slyke and J. Sendroy, Studies of gas and electrolyte equilibrium in blood, J. B. C. Vol. 79, 781–798, 1928; C. Gaudebout, M. C. Blayo and J. J. Pocidalo, A comparative study of techniques for direct and indirect determinations of blood $pCO_2$). The chemical interaction of respiratory gases with dog blood was assumed to be similar to that for human blood. A Travenol-Sarns hemodialysis pump was calibrated and used to estimate extracorporeal blood flow. Using blood flow rate and the $CO_2$ content estimates on whole blood going to and from the artificial kidney, $CO_2$ transport was determined, the results of which are given in FIG. 3.

These $CO_2$ transfer estimates were obtained using several types of commercially available dialysis coils and flat plate and hollow fiber kidneys. No substantial advantage of using one type of dialyzer over another was noted though flat plate and hollow fiber artificial kidneys were easier to use because of the associated lower pressure drop and decreased ultrafiltration. $CO_2$ transfer estimates were obtained using dialysis bath addition flow rates of from 100 to 1000 ml per min. These $CO_2$ transfer estimates are intended to provide an overall estimate of $CO_2$ transfer capability using hemodialysis.

Higher $CO_2$ transfers were obtained using addition of $Ca(OH)_2$ ($5.7 \pm 0.5$ S. E. mMoles $CO_2$ per min.) rather than NaOH ($2.7 \pm 0.2$ S. E. mMoles $CO_2$ per min.) to the dialysis bath, as shown in FIG. 3. The higher transfers of $CO_2$ associated with $Ca(OH)_2$ can be attributed to a more favorable chemical concentration gradient for bicarbonate ion achieved by rapid conversion of bicarbonate ion to calcium carbonate precipitate. However, the superiority of the $Ca(OH)_2$ over the NaOH alkali addition system was apparent only during the first two hours of hemodialysis.

Total oxygen consumption was determined for each experiment using a Collins spirometer 14. Assuming a respiratory quotient of 0.9, $CO_2$ production for the entire experiment could be estimated and generally confirmed the estimate of $CO_2$ production based on the $CO_2$ transfer determinations given in FIG. 3.

The Collins spirometer also provided a continuous recording of respiratory rate and minute ventilation during each experiment. These two parameters proved to be appropriate, predictable, and sensitive indicators of blood pH, and $pCO_2$. If a dog was dialyzed too aggressively, then his $pCO_2$ fell and he became alkalotic and his minute ventilation and respiratory rate slowed or, in extreme cases, stopped. However, upon slowing hemodialysis, either by decreasing extracorporeal blood flow, or decreasing the addition of fresh alkaline dialysis solution, the ventilation would return to normal. Conversely, if the dog was not dialyzed aggressively enough, then ventilation and respiratory rate would increase, and would therefore require increased hemodialysis to return pH and $pCO_2$ to baseline, or at least prevent a further increase.

Clearance of 2–6 millimoles of $CO_2$ per minute, or about half the basal $CO_2$ excretion for a hypothetical 70 Kg man can thus be achieved using commercially available hollow fiber kidney and dialysis coils designed for human use. Higher extracorporeal blood flow rates up to 750 ml/min and addition of sufficient alkali to the dialysis bath recipe to obtain a hydroxyl ion concentration of about 1 to 10 milliequivalents/liter (pH 11–12) are necessary. The regenerated cellulose, of which commercial dialysis membranes are made, tolerates the exposure to this degree of alkalinity and the increased pressures associated with increased blood flow rate, as indicated by the fact that 12 consecutive dialysis coils were used each for a matter of hours without blood leakage or rupture.

During conventional hemodialysis for renal failure, calcium and magnesium ion are added to the hemodialysis bath to prevent hypocalcemia and hypomagnesia. However, both of these ions precipitate upon addition of alkali and bicarbonate ion. Therefore, when $CO_2$ excretion is the goal of the dialysis procedure, then calcium and magnesium ion are not added to the dialysis bath reservoir. Instead, these two ions are infused simultaneously from the same IV bottle directly into the venous return line at a rate of 0.0077 and 0.0045 mEg/min/Kg for calcium and magnesium respectively.

Phosphate was also lost during dialysis and replaced intravenously at a rate of 0.001 mEg of phosphoric acid/min/Kg as a physiological saline solution made 1% with respect to phosphoric acid. Phosphate infusion was made at a different infusion site than that used for calcium and magnesium ion infusion so as to prevent precipitation from these solutions.

The infusion rates necessary to replace the calcium, magnesium, and phosphate lost in the hemodialysis bath were determined empirically by serially measuring plasma calcium, and inorganic phosphorus (Technicon Autoanalyzer Method) and magnesium (by atomic absorption).

It will be apparent from the foregoing that I have provided a simple and effective means for the removal of carbon dioxide from blood plasma without undesirable alteration of pH levels of the blood and that such carbon dioxide removal means may be employed in combination with an oxygenator for the simultaneous supply of oxygen to the blood plasma to achieve simultaneous heart and lung function.

It will be understood that changes may be made in the details of construction and operation without departing from the spirit of the invention, especially as defined in the following claims.

I claim:

1. The method of removing carbon dioxide from whole blood by dialysis comprising the steps of bypassing the blood from the blood stream circulated through the human system, passing the bypassed blood into contact with one side of a hemodialysis membrane which allows for the dialysis while the other side is wet by contact with an aqueous electrolyte containing an alkaline material in solution in an amount sufficient to make free hydroxyl ions available for transport through the membrane whereby carbon dioxide, which is formed in the blood and combines with water in accordance with the equation $H_2O + CO_2 \rightarrow H_2CO_3 \rightarrow HCO_3^- + H^+$ is removed from the blood stream by transport of bicarbonate ion through the membrane to the aqueous electrolyte while hydroxyl ions transport from the electrolyte through the membrane to neutralize hydrogen ions which remain in the blood, and in which the alkaline material is present in the electrolyte in an amount to maintain the normal level of blood pH in which the alkaline material is selected from the group consisting of an alkali metal hydroxide and an alkaline earth metal hydroxide.

2. The method as claimed in claim 1 in which the alkali is a combination of sodium hydroxide and calcium hydroxide in solution in aqueous medium.

3. The method as claimed in claim 2 in which the amount of calcium hydroxide is less than the stoichiometric amount required for reaction with the bicarbonate ion transferred through the membrane into the electrolyte.

4. The method of removing carbon dioxide from whole blood by dialysis comprising the steps of bypassing blood from the blood stream circulating through the human system, passing the bypassed blood into contact with one side of a hemodialysis membrane which allows for the dialysis while the other side is wet by contact with an aqueous electrolyte containing an alkaline material selected from the group consisting of alkali metal hydroxide and alkaline earth metal hydroxide in solution in an amount sufficient to maintain a pH within the range of 10 to 13 to make free hydroxyl ions available for transport through the membrane whereby carbon dioxide, which is formed in the blood and combines with water in accordance with the equation $H_2O + CO_2 \rightarrow H_2CO_3 \rightarrow HCO_3^- + H^+$ is removed from the blood stream by transport of bicarbonate ion through the membrane to the aqueous electrolyte while hydroxyl ions transport from the electrolyte through the membrane to neutralize hydrogen ions which remain in the blood, and in which the alkaline material is present in the electrolyte in an amount to maintain the normal level of blood pH.

5. The method as claimed in claim 4 which includes the step of bubbling air or oxygen through the electrolyte for removal of carbon dioxide.

6. The method as claimed in claim 4 which includes the step of simultaneous oxygenation of the blood by utilization of a dialysis membrane which contains a catalyst for conversion of hydrogen peroxide to oxygen during transport of hydrogen peroxide into the membrane and in which hydrogen peroxide is present in dilute solution in the electrolyte.

7. The method as claimed in claim 4 in which the dialysis membrane is a hydrophilic cellulose derivative.

8. The method as claimed in claim 6 in which the catalyst is selected from the group consisting of manganese oxide and cobalt, lead, nickel, iron and osmium oxide and hydroxide.

9. The method as claimed in claim 4 in which the alkaline material is present in the electrolyte in an amount to maintain the pH of the blood within the range of 7.2 to 7.35.

10. The method as claimed in claim 4 in which the alkaline material in the electrolyte is present in an amount to maintain the $pCO_2$ of the blood within the range of 45 to 58 mm Hg.

* * * * *